United States Patent [19]

Gerhart et al.

[11] Patent Number: 5,259,701

[45] Date of Patent: Nov. 9, 1993

[54] ANTIFOULING COATING COMPOSITION COMPRISING FURAN COMPOUNDS, METHOD FOR PROTECTING AQUATIC STRUCTURES, AND ARTICLES PROTECTED AGAINST FOULING ORGANISMS

[75] Inventors: Donald L. Gerhart, Hillsborough; Daniel Rittschof, Morehead City; Irving R. Hooper, Beaufort; Anthony Clare, Morehead City, all of N.C.

[73] Assignee: Rohm and Haas Company, Philadelphia, Pa.

[21] Appl. No.: 964,795

[22] Filed: Oct. 22, 1992

[51] Int. Cl.⁵ .................................................. C02F 1/50
[52] U.S. Cl. ...................................... 405/216; 405/211; 106/15.05; 106/18.32; 106/18.33; 106/18.34; 106/18.35; 514/468; 514/470; 514/473; 514/461; 514/471; 514/455; 424/78.09; 210/749; 210/764; 210/698; 427/385.5; 427/393; 427/389.9; 427/372.2; 252/180; 252/181
[58] Field of Search .............. 106/15.05, 18.32–18.35; 71/66, 67, 88; 514/468, 470, 473, 461, 471, 455; 424/78.09; 210/749, 764, 698; 252/180, 181; 405/211, 216; 427/385.5, 393, 389.9, 372.2

[56] References Cited

U.S. PATENT DOCUMENTS

| | | | |
|---|---|---|---|
| 4,410,642 | 10/1983 | Layton et al. | 523/122 |
| 4,596,724 | 6/1986 | Lane et al. | 106/15.05 |
| 4,788,302 | 11/1988 | Costlow et al. | 106/15.05 |
| 4,923,894 | 5/1990 | Kanda et al. | 524/461 |
| 5,128,370 | 7/1992 | Grabley et al. | 514/473 |
| 5,154,747 | 10/1992 | Yokoi et al. | 106/15.05 |

FOREIGN PATENT DOCUMENTS

| | | | |
|---|---|---|---|
| 52-10911 | 9/1977 | Japan . | |
| 44018A | 4/1979 | Japan . | |
| 130905 | 10/1980 | Japan | 106/15.05 |
| 1519882 | 8/1978 | United Kingdom | 106/15.05 |
| 2006183 | 5/1979 | United Kingdom | 106/15.05 |

OTHER PUBLICATIONS

Journal of Chemical Ecology, vol. 14, No. 10, 1988, Gerhart et al., pp. 1905–1917.
Journal of Chemical Ecology, vol. 16, No. 3, 1990, Gerhart et al., pp. 791–799.
J. Exp. Mar. Biol. Ecol., 1984, vol. 82, Rittschoff et al., pp. 131–146.

*Primary Examiner*—Stanley S. Silverman
*Assistant Examiner*—Neil M. McCarthy
*Attorney, Agent, or Firm*—Michael B. Fein

[57] ABSTRACT

Certain furan compounds are disclosed as being useful as marine or fresh water antifoulant compounds to be used in protective carrier compositions such as film forming polymer to protect fish nets, boats, pilings, and piers.

13 Claims, No Drawings

ANTIFOULING COATING COMPOSITION COMPRISING FURAN COMPOUNDS, METHOD FOR PROTECTING AQUATIC STRUCTURES, AND ARTICLES PROTECTED AGAINST FOULING ORGANISMS

BACKGROUND OF THE INVENTION

This invention relates generally to protection of underwater surfaces from fouling by aquatic organisms. This invention was made with government support awarded by the Office of Naval Research under contract No. N00014-86-K-0261. The government has certain rights in the invention.

DESCRIPTION OF THE PRIOR ART

In marine, brackish, and freshwater environments, organisms collect, settle, attach, and grown on submerged structures. Organisms which do so can include algae, and aquatic animals, such as tunicates, hydroids, bivalves, bryozoans, polychaete worms, sponges, and barnacles. Submerged structures can include the underwater surfaces of ships, docks and piers, pilings, fishnets, heat exchangers, dams, piping structures, such as intake screens, and cooling towers. The presence of these organisms, known as the "fouling" of a structure, can be harmful in many respects. They can add to the weight of the structure, hamper its hydrodynamics, reduce its operating efficiency, increase susceptibility to corrosion, and degrade or even fracture the structure.

The common method of controlling the attachment of fouling organsims is by protecting the structure to be protected with a paint or coating which contains an antifouling agent. Exemplary antifouling coatings and paints are described in U.S. Pat. No. 4,596,724 to Lane, U.S. Pat. No. 4,410,642 to Layton, and U.S. Pat. No. 4,788,302 to Costlow. Application of a coating of this type inhibits the attachment, or "settling", of the organism, by either disabling the organism or providing it with an unattractive environment upon which to settle.

Of the fouling organisms noted above, barnacles have proven to be among the most difficult to control. Typically, commercial antifouling coatings and paints include a toxic metal-containing compound such as tri-n-butyl tin (TBT), or cuprous oxide, which leaches from the coating. Although these compounds exhibit moderate success in inhibiting barnacle settlement, they degrade slowly in marine enviornments, and therefore are ecologically harmful. In fact, TBT is sufficiently toxic that its release rate is limited by legislation in some countries.

Some experimental non-toxic compounds have been tested with limited success in barnacle settlement inhibition. See, e.g., Gerhart et al., J. Chem. Ecol. 14:1905-1917 (1988), which discloses the use of pukalide, epoxypulkalide, and an extract produced by the octocoral *Leptogorgia virgulata*, to inhibit barnacle settlement, and Sears et al., J. Chem. Ecol. 16:791-799 (1990), which discloses the use of ethyl acetate extracts of the sponge *Lissodendoryx isodictylais* to inhibit settlement.

Japanese Patent Disclosure No. 54-44018A of Apr. 7, 1979 (Patent Application No. 52-109110 of Sep. 10, 1977, discloses gamma-methylenebutenolide lactone and alkyl gamma-methylenebutenolide lactone derivatives having the general structure

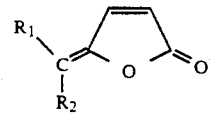

wherein $R_1$ and $R_2$ are hydrogen or saturated or unsaturated alkyl groups of 1-8 carbon atoms. The compounds are natural products from terrestrial plants.

In view of the foregoing, it is an object of the present invention to provide an antifouling composition which is effective in inhibiting the settlement of fouling organisms on an underwater surface.

Another object of the present invention is to provide an antifouling paint or coating composition which is effective in protecting underwater structures from fouling by barnacles, and other aquatic organisms.

A further object is to provide structures which are effectively protected against fouling by aquatic organisms.

SUMMARY OF THE INVENTION

These and other objects are accomplished by the present invention which in one aspect comprises a composition for use as a marine or freshwater antifoulant comprising a protective carrier component functioning to release antifouling agent and, as an antifouling agent, at least one furan compound of Formula I or II

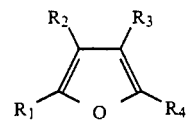

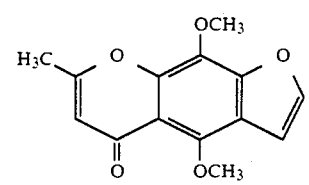

wherein $R_1$, $R_2$, $R_3$, and $R_4$ are independently selected from $-C(O)R_5$, $-C(O)OR_6$, $(C_1-C_8)$alkyl, phenyl, phenyl substituted with $(C1-C_4)$alkyl, $(C_1-C_4)$alkoxy, $(C_2-C_8)$alkenyl, $(C_2-C_8)$alkynyl, halogen, and hydrogen, provided that at least one of $R_1$, $R_2$, $R_3$, and $R_4$ is not hydrogen; $R_5$ is $R_6$ or $NR_7R_8$; $R_6$ is $(C_1-C_8)$alkyl, $(C_2-C_8)$alkenyl, $(C_2-C_8)$alkynyl, phenyl, phenyl substituted with $(C_1-C_4)$alkyl, $(C_1-C_4)$alkoxy, or halogen; $R_7$ and $R_8$ are independently selected from hydrogen or $R_6$.

A second aspect of the present invention comprises a method of protecting a marine or freshwater structure against fouling by marine or freshwater fouling organisms comprising applying a compound of Formula I or II on and/or into said structure.

Another invention is a marine or freshwater structure protected against fouling organisms wherein said protection is afforded by at least one furan compound of Formula I or II having been applied on and/or into said structure.

DETAILED DESCRIPTION OF THE INVENTION

The present invention is directed to controlling the attachment of unwanted organisms to submerged surfaces by contacting the organisms with an antifouling compound of Formula I or II. It has been discovered that furan compounds of Formula I or II inhibit the settlement of fouling organisms, particularly barnacles. As used herein, "settlement" refers the attachment of aquatic organisms to an underwater structure. Contacting an organism with a compound of Formula I or II in the area adjacent a submerged surface prevents the settling of the organism on that submerged surface.

In the practice of the method of the present invention, the antifouling compound may be contacted to the organism by coating the object to be protected with a coating containing the antifouling compound, which then releases the compound into the aquatic environment immediately adjacent the external surfaces of the article, by including the antifouling compound within material formed into an aquatic article which then releases the compound, by releasing the compound directly into the aquatic environment surrounding the protected object, or by any other method wherein the compound contacts the organism prior to its attachment to the surface. As used herein, the term "contacting" means that an amount of antifouling compound sufficient to inhibit settlement of the organism on the surface of interest physically contacts the organism, whether by direct external contact, inhalation, respiration, digestion, inhibition, or any other process.

Preferred furan compounds are 2-ethylfuran; 2-methylfuran; methyl-2-furanoate; ethyl-3-furoate; 2-furyl-n-pentyl ketone; 2-acetylfuran; and khellin (Formula II).

The amount of compound to be used in the method will vary depending on a number of factors, including the identity of the antifouling compound, the identity of the organism to be inhibited, and the mode of contact. In addition, the rate at which the compound is released into the surrounding aquatic environment can be a major factor in determining both the effectiveness of the method and the duration of protection. If the compound is released too rapidly, it will be exhausted quickly, and the coating must be re-applied for the surface to be protected. If on the other hand the release rate of the antifouling compound is too slow, the concentration of the compound in the aquatic environment immediately surrounding the surface to be protected may be insufficient to inhibit settlement. Preferably, the antifouling compound is released into the environment adjacent the protected surface at the rate of between about 0.0001 and 1000 $\mu g/cm^2$-hr, and more preferably is released at a rate of between about 0.01 and 100 $\mu g/cm^2$-hr. Compositions of the invention preferably comprise furan compound(s) in a concentration of about 0.01 weight percent to about 50 weight percent based on said composition, more preferably in a concentration of about 0.1 to 20 weight percent based on said composition.

The organisms against which a surface can be protected by the present method can be any organism which can attach to a submerged surface. Exemplary organisms include algae, including members of the phyla Chlorophyta and Phaeophyta, fungi, microbes, tunicates, including members of the class Asciidiancea, such as *Ciona intestinalis, Diplosoma listerianium*, and *Botryllus sclosseri*, members of the class Hydrozoa, including *Clava squamata, Hydractinia echinata, Obelia geniculata*, and *Tubularia larnyx*, bivalves, including *Mytilus edulis, Crassostrea virginica, Ostrea edulis, Ostrea chilensia*, and *Lasaea rubra*, bryozoans, including *Ectra pilosa, Bugula neritinia*, and *Bowerbankia gracilis*, polychaete worms, including *Hydroides norvegica*, sponges, and members of the class Cirripedia (barnacles), such as *Balanus amphitrite, Lepas anatifera, Balanus balanus, Balanus balanoides, Balanus hameri, Balanus crenatus, Balanus improvisus, Balanus galeatus*, and *Balanus eburneus*. Organisms of the genus Balanus are particularly frequent foulers of aquatic structures. Specific fouling organisms to which this invention is especially directed include barnacles, zebra mussels, algae, bacteria, diatoms, hydroids, bryzoa, ascidians, tube worms, and asiatic clams.

In addition to the lactone compound, the composition can comprise additional antifouling agents which may act in combination or synergistically; said additional antifouling agent can be, for example: manganese ethylene bisdithiocarbamate; a coordination product of zinc ion and manganese ethylene bisdithiocarbamate; zinc ethylene bisdithiocarbamate; zinc dimethyl dithiocarbamate; 2, 4, 5, 6-tetrachloroisophthalonitrile; 2-methylthio-4-t-butylamino-6-cyclopropylamino-s-triazine; 3-(3,4-dichlorophenyl)-1,1-dimethyl urea; N-(fluorodichloromethylthio)-phthalimide; N,N-dimethyl-N'-phenyl-(N-fluorodichloromethylthio)-sulfamide; tetramethylthiuram disulfide; 2, 4, 6-trichlorophenyl maleimide; zinc 2-pyridinthiol-1-oxide; copper thiocyanate; Cu-10% Ni alloy solid solution; and 4,5-dichloro-2-n-octyl-4-isothiazolin-3-one.

The protective carrier component functioning to release antifouling agent can be a film-forming component, an elastomeric component, vulcanized rubber, or a cementitious component. The protective carrier component can be any component or combination of components which is applied easily to the surface to be protected, adheres to the submerged surface to be protected, and permits the release of the antifouling compound into the water immediately surrounding the coated surface. Different components will be preferred depending on the material comprising the underwater surface, the operation requirements of the surface, the configuration of the surface, and the antifouling compound. Exemplary film-forming components include polymer resin solutions. Exemplary polymer resins include unsaturated polyester resins formed from (a) unsaturated acids and anhydrides, such as maleic anhydride, fumaric acid, and itaconic acid; (b) saturated acids and anhydrides, such as phthalic anhydride, isophthalic anhydride, terephthalic anhydride, tetrahydrophthalic anhydride, tetrahalophthalic anhydrides, chlorendic acid, adipic acid, and sebacic acid; (c) glycols, such as ethylene glycol, 1,2 propylene glycol, dibromoneopentyl glycol, Dianol 33 ®, and Dianol 22 ®; and (d) vinyl monomers, such as styrene, vinyl toluene, chlorostyrene, bromostyrene, methylmethacrylate, and ethylene glycol dimethacrylate. Other suitable resins include vinyl ester-, vinyl acetate-, and vinyl chloride-based resins, elastomeric components, vulcanized rubbers, and urethane-based resins. The cementitious compounds are used to protect certain types of underwater structures, as are the elastomeric materials and vulcanized rubber.

The percentage of the antifouling compound of Formula I or II in the coating required for proper release of the compound into the aquatic environment surrounding the surface to be protected will vary depending on the identify of the antifouling compound, the identity of the film-forming component of the coating and other additives present in the coating which may affect release rate. As described above, the release rate of the antifouling compound can be a major factor in determining both the effectiveness of the method and the duration of protection. It is preferred that the coating be released into the surrounding water at a rate of between about 0.0001 and 1,000 $\mu g/cm^2$-hr; more preferably, the compound comprises between about 0.01 and 100 $\mu g/cm^2$-hr. Preferably, the antifouling compound comprises between about 0.001 and 80 percent of the coating by weight, and more preferably comprises between 0.01 and 20 percent of the coating.

Those skilled in this art will appreciate that a coating of the present invention can comprise any number of forms, including a paint, a gelcoat, or varnish, and the like. The coating can include components in addition to the antifouling coating and film-forming component which confer a desirable property, such as hardness, strength, rigidity, reduced drag, impermeability, or water resistance.

The present invention encompasses any article which contains a surface coated with a coating containing a compound of Formula I or II. Those articles which are particularly suitable for protection with the coating are those which, either intentionally or inadvertently, are submerged for a least the duration required for an organism to settle on a submerged object. Coated articles can comprise any material to which aquatic organisms are know to attach, such as metal, wood, concrete, polymer, and stone. Exemplary articles which may require antifouling protection include boats and boat hulls, fish nets, recreational equipment, such as surfboards, jet skis, and water skis, piers and pilings, buoys, off-shore oil rigging equipment, and decorative or functional stone formations.

The composition of the invention can be a cementitious composition which includes at least one of said antifouling compounds and a cementitious matrix. Such a composition is suitable for use in submerged structures, such as piers, pilings, and offshore oil rigging equipment and scaffolding, upon which fouling organisms tend to settle. Exemplary cementitious matrix compositions include portland cement and calcium aluminate based compositions. As those skilled in this art will appreciate, the cementitious matrix should be able to release the antifouling compound, and the antifouling compound must be present in sufficient concentration that the release rate of the compound into the surrounding aquatic environment inhibits settling of organisms on the submerged surface of an article formed from the composition.

The invention is now described in more detail in the following examples which are provided to more completely disclose the information to those skilled in this art, but should not be considered as limiting the invention.

EXAMPLES

Collection and Culture of Experimental Specimens

Adult individuals of the acorn barnacle *Balanus amphitrite* Darwin were collected from the Duke University Marine Laboratory seawall in Beaufort, N.C. Collected specimens were crushed, and the nauplius stage larvae released therefrom were cultured to cyprid stage for cyprid-stage assays according to the methods of Rittschof et al., *J. Exp. Mar. Biol. Ecol.* 82:131-146 (1984).

Settlement Assay for Cyprid-Stage Larvae

Settlement assays were performed as previously described by Rittschof et al. *J. Chem. Ecol.* 11:551-563 (1985). Three-day old cyprid larvae were used.

All compounds were tested for their ability to inhibit settlement by cyprid larvae of the barnacle *Balanus amphitrite*. Larvae were added to 50×9 mm polystyrene Petri dishes containing 5 ml of aged seawater that had been passed through a 100 kDa cut-off filter and varying levels of test compound. Controls consisted of barnacle larvae and filtered seawater added to the dishes without test compound. Dishes were then incubated for 20-24 hrs at 28° C. with light for approximately 15 hours and in darkness for approximately 9 hours. The dishes were then removed from the incubator, examined under a dissecting microscope to determine whether larvae were living or dead. Larvae were then killed by addition of several drops of 10% formalin solution. Settlement rate was quantified as number of larvae that had attached to the dish surface, expressed as a percentage of total larvae in the dish. Experiments were performed in duplicate. The lower the percent settlement, the more efficacious the test compound.

EXAMPLE 1

Ethyl-3-furoate (9.63 $\mu l$) was diluted to 20 ml with seawater. Aliquots of this stock solution were added to separate dishes containing seawater to provide the concentrations shown in Table 1. The larvae were added and the test conducted as described above.

TABLE 1

| Control of Barnacle Settlement with Ethyl-3-furoate | |
|---|---|
| Concentration | % Settlement |
| 0 (Control) | 53 |
| 500 µg/ml | 0 |
| 50 µg/ml | 11 |
| 5 µg/ml | 18 |
| 500 ng/ml | 52 |

EXAMPLE 2

Methyl-2-furoate (8.48 $\mu l$) was diluted to 20 ml with seawater. Aliquots of this stock solution were added to separate dishes containing seawater to provide the concentrations shown in Table 2. The larvae were added and the test conducted as described above.

TABLE 2

| Control of Barnacle Settlement with Methyl-2-furoate | |
|---|---|
| Concentration | % Settlement |
| 0 (Control) | 53 |
| 500 µg/ml | 2 |
| 50 µg/ml | 46 |
| 5 µg/ml | 53 |

EXAMPLE 3

2-Ethylfuran (6.94 $\mu l$) was diluted to 20 ml with seawater. Aliquots of this stock solution were added to separate dishes containing seawater to provide the concentrations shown in Table 3. The larvae were added and the test conducted as described above.

TABLE 3

| Control of Barnacle Settlement with 2-Ethylfuran | |
|---|---|
| Concentration | % Settlement |
| 0 (Control) | 53 |
| 500 μg/ml | 41 |
| 50 μg/ml | 54 |

EXAMPLE 4

2-Methylfuran (10.98 μl) was diluted to 20 ml with seawater. Aliquots of this stock solution were added to separate dishes containing seawater to provide the concentrations shown in Table 4. The larvae were added and the test conducted as described above.

TABLE 4

| Control of Barnacle Settlement with 2-Methylfuran | |
|---|---|
| Concentration | % Settlement |
| 0 (Control) | 53 |
| 50 μg/ml | 39 |
| 5 μg/ml | 61 |

EXAMPLE 5

2-Acetylfuran (9.11 μl) was diluted to 20 ml with seawater. Aliquots of this stock solution were added to separate dishes containing seawater to provide the concentrations shown in Table 5. The larvae were added and the test conducted as described above.

TABLE 5

| Control of Barnacle Settlement with 2-Acetylfuran | |
|---|---|
| Concentration | % Settlement |
| 0 (Control) | 53 |
| 500 μg/ml | 54 |

EXAMPLE 6

2-Furyl-n-pentyl ketone (0.909 μl) was diluted to 20 ml with seawater. Aliquots of this stock solution were added to separate dishes containing seawater to provide the concentrations shown in Table 6. The larvae were added and the test conducted as described above.

TABLE 6

| Control of Barnacle Settlement with 2-Furyl-n-pentyl ketone | |
|---|---|
| Concentration | % Settlement |
| 0 (Control) | 42 |
| 500 μg/ml | 0 |
| 50 μg/ml | 1 |
| 5 μg/ml | 2 |
| 500 ng/ml | 14 |
| 50 ng/ml | 26 |
| 5 ng/ml | 20 |
| 500 pg/ml | 22 |

EXAMPLE 7

2-Furyl-n-pentyl ketone (0.909 μl), 2-ethylfuran (6.94 μl) and 2-acetylfuran (9.11 μl) were each diluted to 20 ml with seawater. Aliquots of these stock solutions were added to separate dishes containing seawater to provide the respective test substances in concentrations of 500 μg/ml. The larvae were added and the test conducted as described above. These data are presented in Table 7.

TABLE 7

| Control of Barnacle Settlement with Furan Compounds at 500 μg/ml | |
|---|---|
| Compound | % Settlement |
| Control | 61 |
| 2-Furyl-n-pentyl ketone | 0 |
| 2-Ethylfuran | 34 |
| 2-Acetylfuran | 41 |

While the invention has been described with reference to specific examples and applications, other modifications and uses for the invention will be apparent to those skilled in the art without departing from the spirit and scope of the invention as defined in the following claims.

We claim:

1. A marine or freshwater antifoulant composition comprising a material selected from the group consisting of film-forming polymer, cementitious material, elastomeric material, and vulcanized rubber an amount of an antifouling agent admixed with said material and effective to be released from said material at an antifouling effective level, said antifouling agent selected from the group consisting of at least one furan compound of Formula I or II

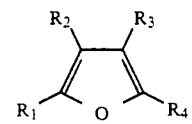

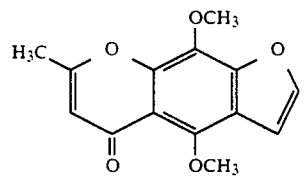

wherein $R_1$, $R_2$, $R_3$, and $R_4$ are independently selected from —$C(O)R_5$, —$C(O)OR_6$, ($C_1$–$C_8$)alkyl, phenyl, phenyl substituted with (C1–C4)alkyl, (C1–C4)alkoxy, halogen, and hydrogen, provided that at least one of $R_1$, $R_2$, $R_3$, and $R_4$ is not hydrogen; $R_5$ is $R_6$ or $NR_7R_8$; $R_6$ is ($C_1$–$C_8$)alkyl, ($C_2$–$C_8$)alkenyl, ($C_2$–$C_8$) alkynyl, phenyl, phenyl substituted with ($C_1$–$C_4$)alkyl, ($C_1$–$C_4$)alkoxy, or halogen; $R_7$ and $R_8$ are independently selected from hydrogen or $R_6$.

2. Composition according to claim 1 wherein said furan compound is present in a concentration of about 0.01 weight percent to about 50 weight percent based on said composition.

3. Composition according to claim 2 wherein said furan compound is present in a concentration of about 0.1 to 20 weight percent based on said composition.

4. Composition according to claim 1 wherein said furan compound is selected from the group consisting of 2-furyl-methylketone; 2-ethyl furan; 2-methyl furan; methyl-2-furanoate; ethyl-3-furoate; 2-furyl-n-pentyl ketone; 2-acetylfuran; and khellin.

5. Composition according to claim 1 further including one or more additional antifouling agents.

6. Composition according to claim 5 wherein said additional antifouling agent is selected from the group consisting of manganese ethylene bisdithiocarbamate; a coordination product of zinc ion and manganese ethylene bisdithiocarbamate; zinc ethylene bisdithiocarbamate; zinc dimethyl dithiocarbamate; 2, 4, 5, 6-tetrachloroisophthalonitrile; 2-methylthio-4-t-butylamino-6-cyclopropylamino-s-triazine; 3- (3,4-dichlorophenyl)-1,1-dimethyl urea; N-(fluorodichloromethylthio)-phthalimide; N,N-dimethyl-N'-phenyl-(N-fluorodichloromethylthio)-sulfamide; tetramethylthiuram disulfide; 2, 4, 6-trichlorophenyl maleimide; zinc 2-pyridin-thiol-1-oxide; copper thiocyanate; Cu-10% Ni alloy solid solution; and 4,5-dichloro-2-n-octyl-4-isothiazolin-3-one.

7. Method of protecting a structure against fouling by marine or freshwater fouling organisms comprising applying a composition according to claim 1 on and/or into said structure.

8. Method according to claim 7 wherein said marine or freshwater fouling organisms are selected from the group consisting of barnacles, zebra mussels, algae, bacteria, diatoms, hydroids, bryzoa, ascidians, tube worms, and asiatic clams.

9. Method according to claim 7 wherein said organisms are one or more members of the genus Balanus.

10. Method according to claim 7 wherein said compound is used in a composition comprising a film-forming polymeric binder.

11. Marine or freshwater structure protected against fouling organisms wherein said protection is afforded by a method according to claim 7.

12. Marine of freshwater structure according to claim 11 wherein said protection is afforded by a composition comprising a film-forming polymeric binder comprising at least one of said furan compounds having been applied on and/or into said structure.

13. Marine or freshwater structure according to claim 11 wherein said structure is a fish net, boat, piling, or pier, or cooling tower.

* * * * *